United States Patent [19]
Nakamura et al.

[11] Patent Number: 5,857,465
[45] Date of Patent: Jan. 12, 1999

[54] BIOSIGNAL DISPLAY APPARATUS

[75] Inventors: Chiaki Nakamura, Chiba; Tsukasa Kosuda, Suwa, both of Japan

[73] Assignees: Seiko Instruments Inc.; Seiko Epson Corporation, both of Japan

[21] Appl. No.: 515,351

[22] Filed: Aug. 15, 1995

[51] Int. Cl.[6] ........................................ A61B 5/02
[52] U.S. Cl. .................. 128/687; 128/689; 128/690
[58] Field of Search .......................... 128/690, 706, 128/733, 687, 731, 732, 664, 665, 608

[56] References Cited

U.S. PATENT DOCUMENTS

| | | | |
|---|---|---|---|
| 3,774,593 | 11/1973 | Hakata | 128/733 |
| 3,978,849 | 9/1976 | Geneen | 128/690 |
| 4,129,124 | 12/1978 | Thalmann | 128/690 |
| 4,579,125 | 4/1986 | Strobl | 128/733 |
| 4,790,326 | 12/1988 | Mather | 128/706 |
| 4,807,639 | 2/1989 | Shimiza | 128/690 |
| 4,823,804 | 4/1989 | Ghislaine | 128/733 |
| 4,938,228 | 7/1990 | Righter | 128/706 |
| 5,029,082 | 7/1991 | Shen et al. | 128/699 |

*Primary Examiner*—John P. Lacyk
*Assistant Examiner*—David Ruddy
*Attorney, Agent, or Firm*—Adams & Wilks

[57] ABSTRACT

A variable accuracy biosignal detector includes a biosignal detector for detecting a biosignal such as a pulse wave from a living body and supplies the detected signal to a biosignal analog-to-digital converter. The analog-to-digital converter converts the biosignal to digital biosignal data values and stores the data in a memory. An input switch generates a start signal. In response to the start signal, a timing signal generating circuit generates a timing signal used as a sampling signal for driving the analog-to-digital converter and changes the sampling frequency of the analog-to-digital converter progressively on a time series basis. A biosignal calculating circuit performs frequency domain analysis when the number of stored digital biosignal data values reaches a predetermined value. By progressively reducing the sampling frequency of the analog-to-digital converter, measured results can be quickly displayed, while the accuracy of the displayed results is progressively increased.

23 Claims, 14 Drawing Sheets

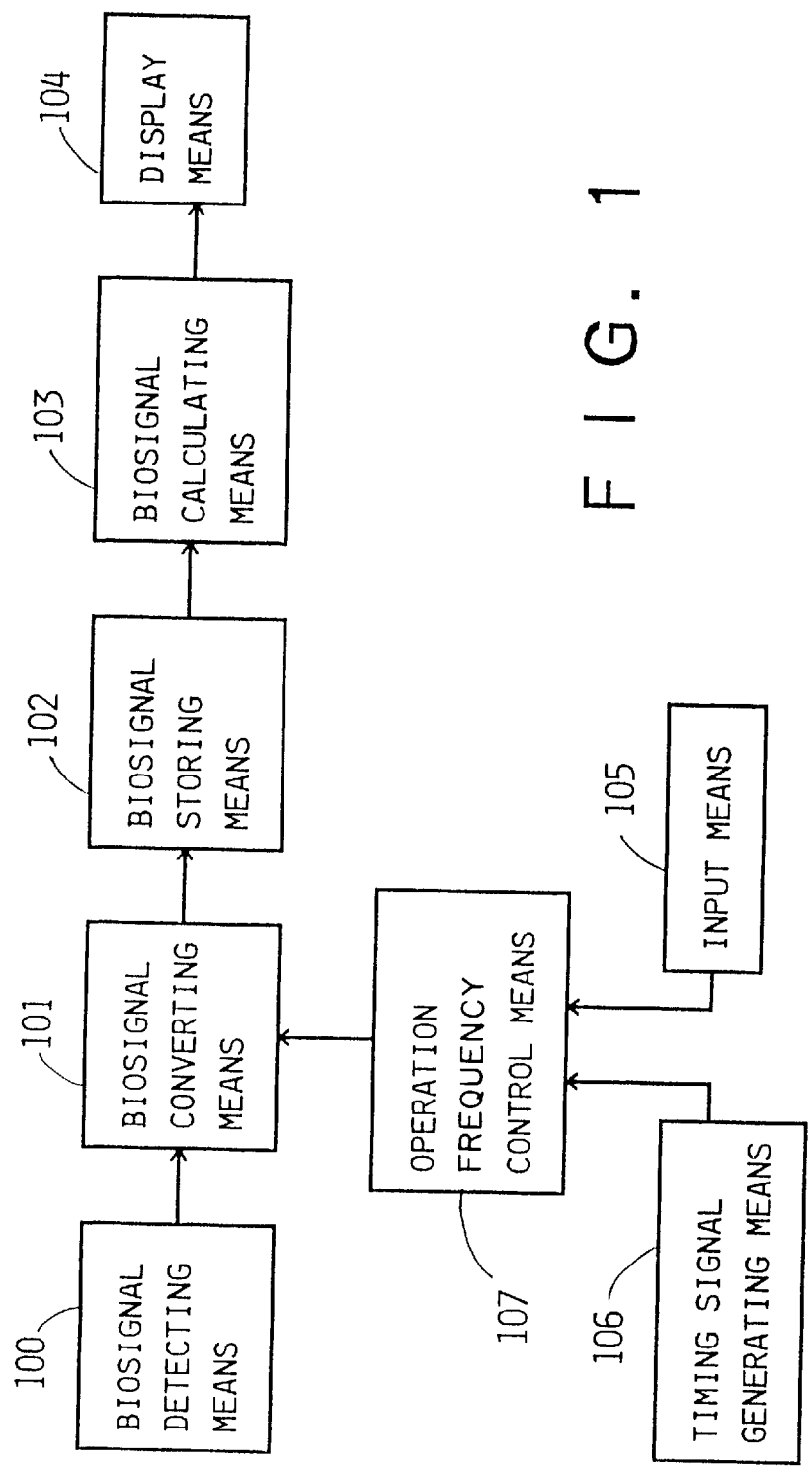
F I G. 1

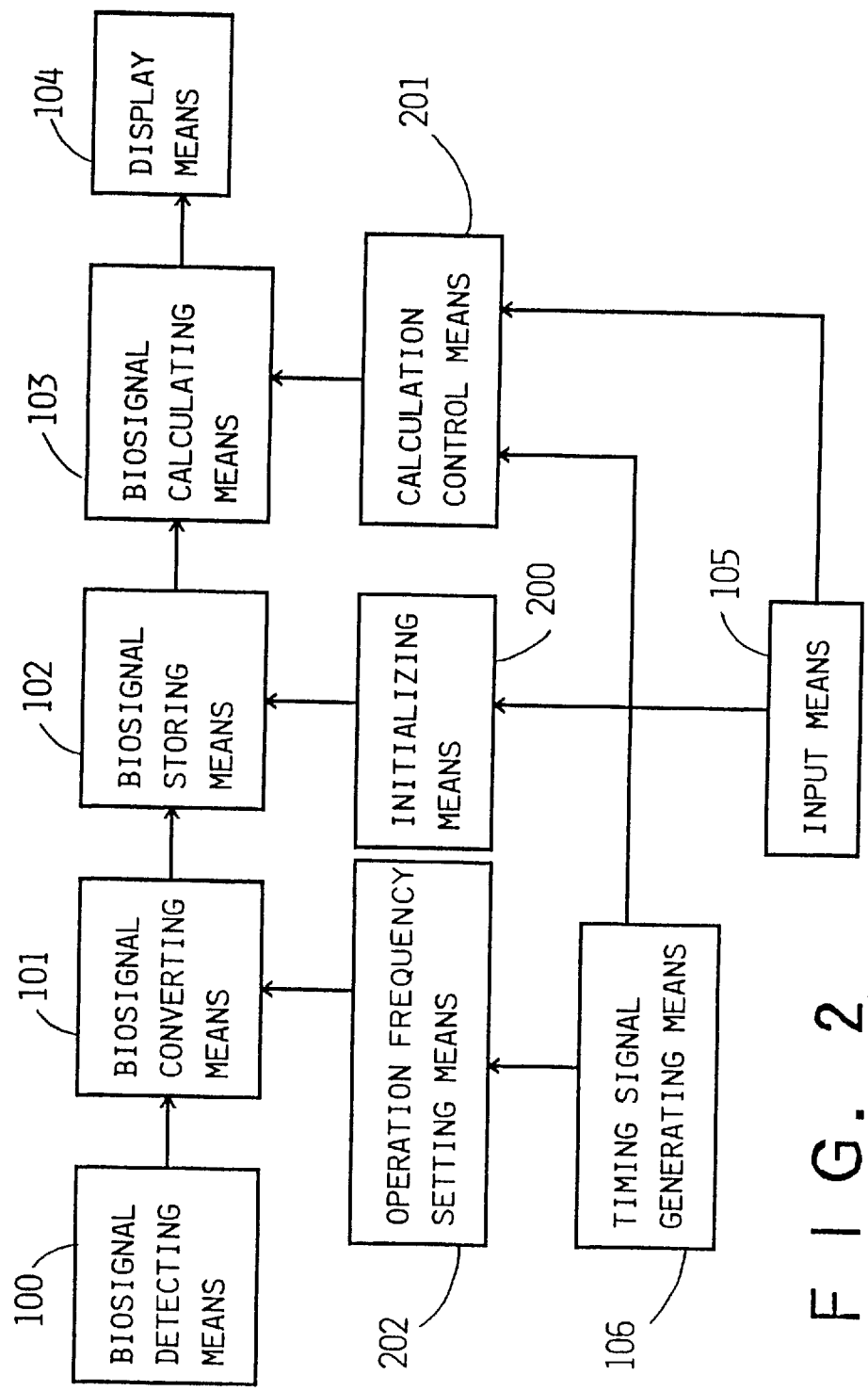
F I G. 2

BIOSIGNAL DISPLAY APPARATUS

BACKGROUND OF THE INVENTION

The present invention relates to a biosignal display apparatus for detecting a biosignal such as a pulse wave and displaying a detection result.

FIG. 3 is a functional block diagram showing the operation of a conventional biosignal display apparatus. A biosignal detecting means 300 detects and amplifies a biosignal such as a pulse wave. A signal converting means 301 performs, at predetermined intervals, analog-to-digital conversion on the biosignal as amplified by the biosignal detecting means 300. A calculation means 302 stores the biosignal as converted by the signal converting means 301, and performs a fast Fourier transform upon storage of $2^n$ data. A display the means 303 displays calculation results of the calculation means 302.

The above type of biosignal display apparatus is disclosed in Japanese Unexamined Patent Publication No. Hei. 1-27534, for instance.

It is generally known to subject a biosignal such as a pulse wave to a fast Fourier transform in analyzing it in the frequency domain. Low-frequency components make up a large part of a biosignal detected from a living body. For example, if frequency-domain analysis is conducted to perform calculation on the interval of a pulse wave, a spectrum will range from 0.5 to 4 Hz. It takes 16 seconds to acquire, for instance, 128 data values that are necessary for frequency-domain analysis by performing analog-to-digital conversion at intervals corresponding to 8 Hz according to the sampling theorem. A calculation resolution of about 3.75 pulses per minute is obtained by performing a general fast Fourier transform under the above condition.

As described above, it takes an excessive time to perform a frequency-domain calculation, with high accuracy, on a biosignal such as a pulse wave using a frequency-domain analyzing technique, and the display of calculation results is delayed. As a result such an apparatus is not convenient to use.

SUMMARY OF THE INVENTION

It is an object of the present invention to provide a biosignal display apparatus which can quickly display results of calculation for processing a biosignal while maintaining sufficient accuracy.

As a first means for solving the above problems, the invention provides a configuration comprising an operation interval control means for changing the operation interval of a biosignal converting means based or a biosignal display start signal that is output from an input means and a timing signal generated by a timing signal generating means.

As a second means for solving the above problems, the invention provides a configuration comprising an initializing means for initializing the biosignals stored in the biosignal storing means in response to the output signal of the input means, an operation interval setting means for setting the operation interval of a biosignal converting means based on a timing signal generated by the timing signal generating means, and a calculation control means for changing, in time series order, the number of biosignals to be subjected to frequency-domain analysis based on a biosignal display start signal that is output from an input means and the timing signal generated by the timing signal generating means, and for causing a biosignal calculating means to operate.

FIG. 1 is a functional block diagram showing an example of typical configurations of the first means described above. A biosignal detecting means 100 detects a biosignal such as a pulse wave from a living body, and supplies the detected signal to a biosignal converting means 101. The biosignal converting means 101 converts the received biosignal to a digital signal, and supplies it to a biosignal storing means 102. The biosignal storing means 102 stores the biosignals as converted to the digital signals by the biosignal converting means 101. An input means 105 outputs a biosignal display s:art signal. A timing signal generating means 106 generates a timing signal by frequency-dividing a basic clock signal. An operation frequency control means 107 receives the display start signal and the timing signal, and progressively changes the operation frequency of the biosignal converting means 101 in time series order. A biosignal calculating means 103 performs calculation of frequency-domain analysis when the number of biosignals stored in the biosignal storing means 102 has reached a predetermined number, and supplies results of the calculation to a display means 104. By causing the operation frequency control means 107 to control the biosignal converting means 101, the operation frequency is short when the display start signal is generated and is thereafter gradually elongated. As a result, calculation results are quickly displayed on the display means 104 while the calculation accuracy of the frequency-domain analysis of the biosignal calculating means 103 is gradually improved.

FIG. 2 is a functional diagram showing another example of the typical configurations of the second means described above. A biosignal storing means 102 stores, as sign-added data having a central value of 0, biosignals as converted to digital signals by a biosignal converting means 101. An initializing means 200 performs initialization by causing the biosignal storing means 102 to store 0 in response to a biosignal display start signal that is output from an input means 105. An operation frequency setting means 202 sets the operation frequency of the biosignal converting means 101 based on a timing signal generated by a timing signal generating means (106). A calculation control means 201 changes, in time series order, the number of biosignals to be subjected to frequency-domain analysis based on the biosignal display start output from the input means 105 and the timing signal generated by the timing signal generating means 106, and causes the biosignal calculating means 103 to operate. Calculation results can be quickly displayed on a display means 104 while the calculation accuracy of the frequency-domain analysis of the bicsignal calculating means 103 is gradually improved by making the number of biosignals to be subjected to the frequency domain analysis small when the display start signal is generated and thereafter increasing it gradually.

BRIEF DESCRIPTION OF THE DRAWINGS

FIG. 1 is a functional block diagram showing an example of a typical configuration of the present invention;

FIG. 2 is a functional block diagram showing an example of another typical configuration of the invention;

DETAILED DESCRIPTION OF THE PREFERRED EMBODIMENTS

Embodiments of the present invention will be hereinafter described in detail based on the drawings.

(1) First Embodiment

Figure 3:
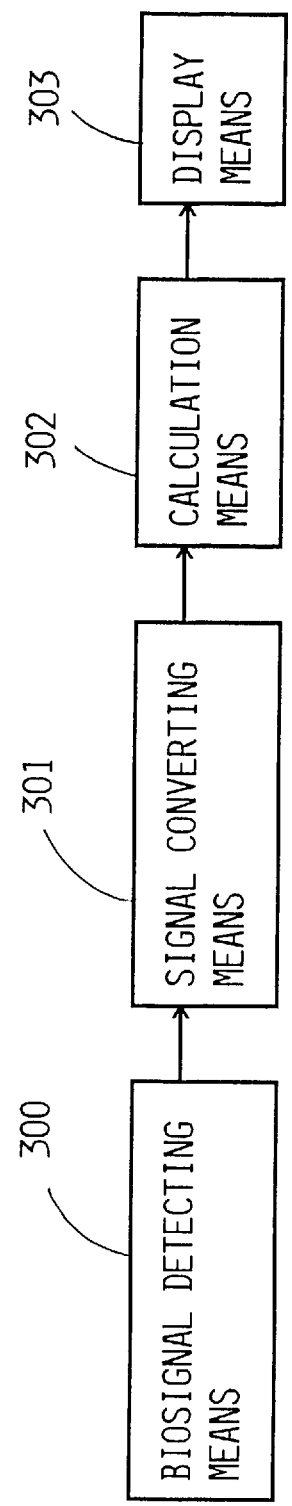
FIG. 3 is a functional block diagram showing the operation of a conventional biosignal display apparatus.
Figure 4:
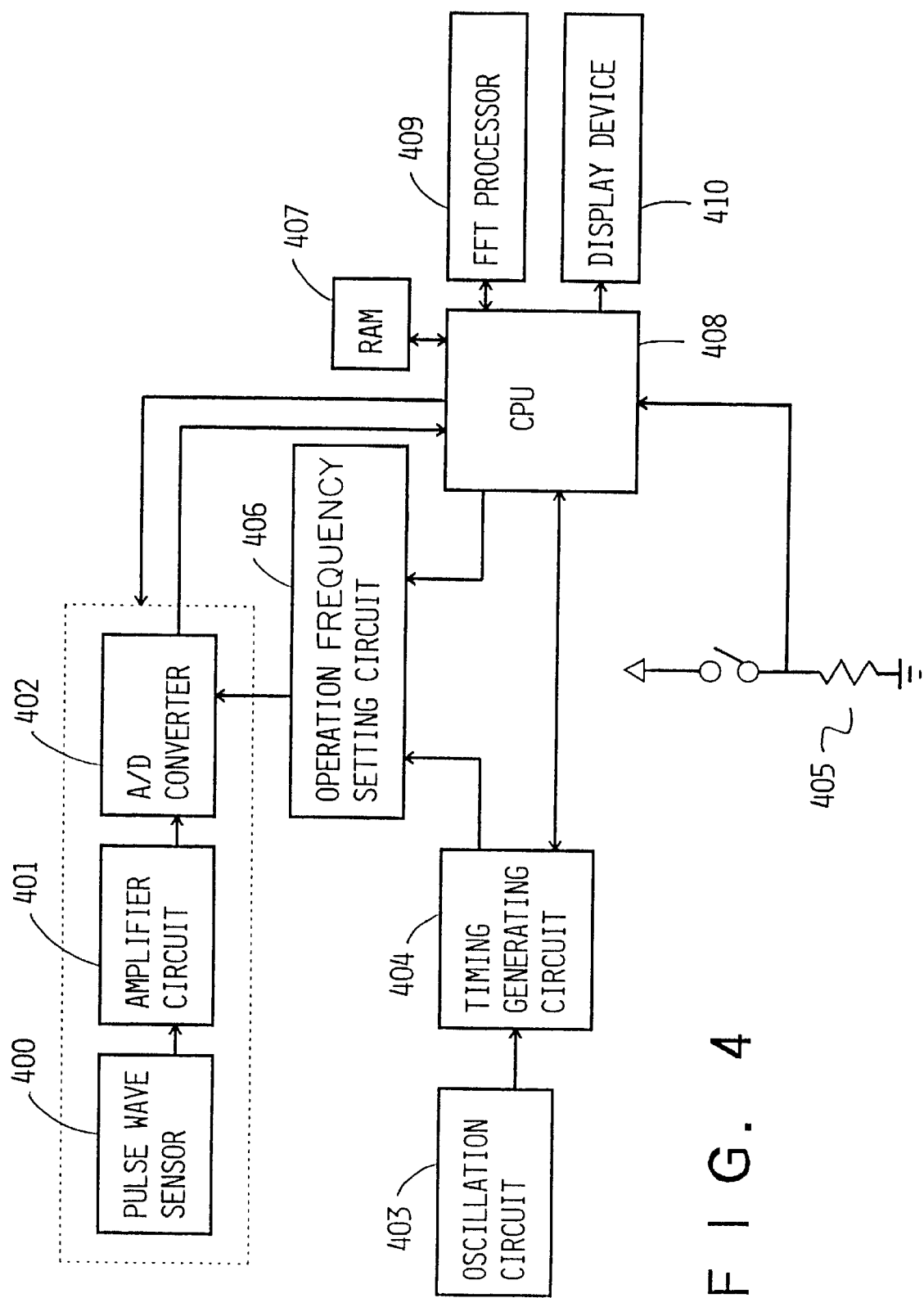
FIG. 4 is a functional block diagram showing a biosignal display apparatus according to an embodiment of the invention.

FIG. 4 is a functional block diagram showing a biosignal display apparatus according to a first embodiment of the invention.

In the following description, although a pulse wave signal is used as an example of a biosignal, the biosignal may be signals indicating a cardiopotential, a brain wave, etc. First, a description will be made of operations of detecting a pulse wave signal, performing FFT (fast Fourier transform) calculation, and displaying its results.

A pulse wave sensor 400 detects a variation in a blood flow by means of an optical means. More specifically, it detects a pulse wave signal reflection light or transmission light originating from a light-emitting element such as a LED with a photodetecting element such as a phototransistor, and supplies the detected pulse wave signal to an amplifier circuit 401. The amplifier circuit 401 performs amplification and filtering on the pulse wave signal, and supplies a resulting signal to an A/D converter 402. The A/D converter 402 converts the! received pulse wave signal to a digital signal, and supplies an interrupt signal to a CPU 408 upon completion of the conversion. When receiving the interrupt signal, the CPU 408 reads the conversion data from the A/D converter 402, and transfers the result to a RAM 407. In doing so, the CPU 408 monitors the RAM 407 to check whether 128 conversion data have been stored in the RAM 407. When 128 conversion data have been stored, the CPU 408 transfers the data to a FFT processor 409 and supplies a FFT calculation instruction to the FFT processor 409. The FFT processor 409 performs FFT processing in response to the calculation instruction. The CPU 408 reads a calculation result from the FFT processor 409, converts it to the number of pulses per minute, and transfers a result to a display device 410. The display device 410, i.e., a liquid crystal device displays the result.

The above operations are operations in the normal mode. Next, a description will be made of operations performed at the start. A switch 405 supplies, as an interrupt signal, a display start signal to the CPU 408 to initiate those operations. Upon reception of the start signal, the CPU 408 supplies power to the pulse wave sensor 400, amplifier circuit 401 and A/D converter 402. Although not illustrated in this embodiment, the CPU 408 stops the supply of power in response to an end signal. The power consumption can be saved by this control. An oscillation circuit 403 contains an oscillator, and supplies an oscillation signal to a timing generating circuit 404. The timing generating circuit 404 not only supplies, an interrupt signal to the CPU 408 but also supplies a plurality of timing signals to an operation frequency setting circuit 406. The CPU 408 resets the timing generating circuit (404) once in response to the display start signal from the switch 405, thereafter enables an interrupt signal, and performs counting until the operation of the pulse wave sensor 400, amplifier circuit 401 and A,/D converter 402 become stable. When judging that the operation has become stable, the CPU 408 supplies the operation frequency setting circuit 406 with data for setting the operation frequency of the A/D converter 402. The operation frequency setting circuit 406 sets the operation frequency of the A/D converter 402 based on the timing signal sent from the timing generating circuit 404 and the operation frequency setting data sent from the CPU 408. In doing so, the CPU 408 progressively changes, in time series order, the operation frequency setting data that are supplied to the operation frequency setting circuit 406. For example, the conversion frequency is varied in a time series order of 32 Hz, 16 Hz and 8 Hz.

Figure 5:
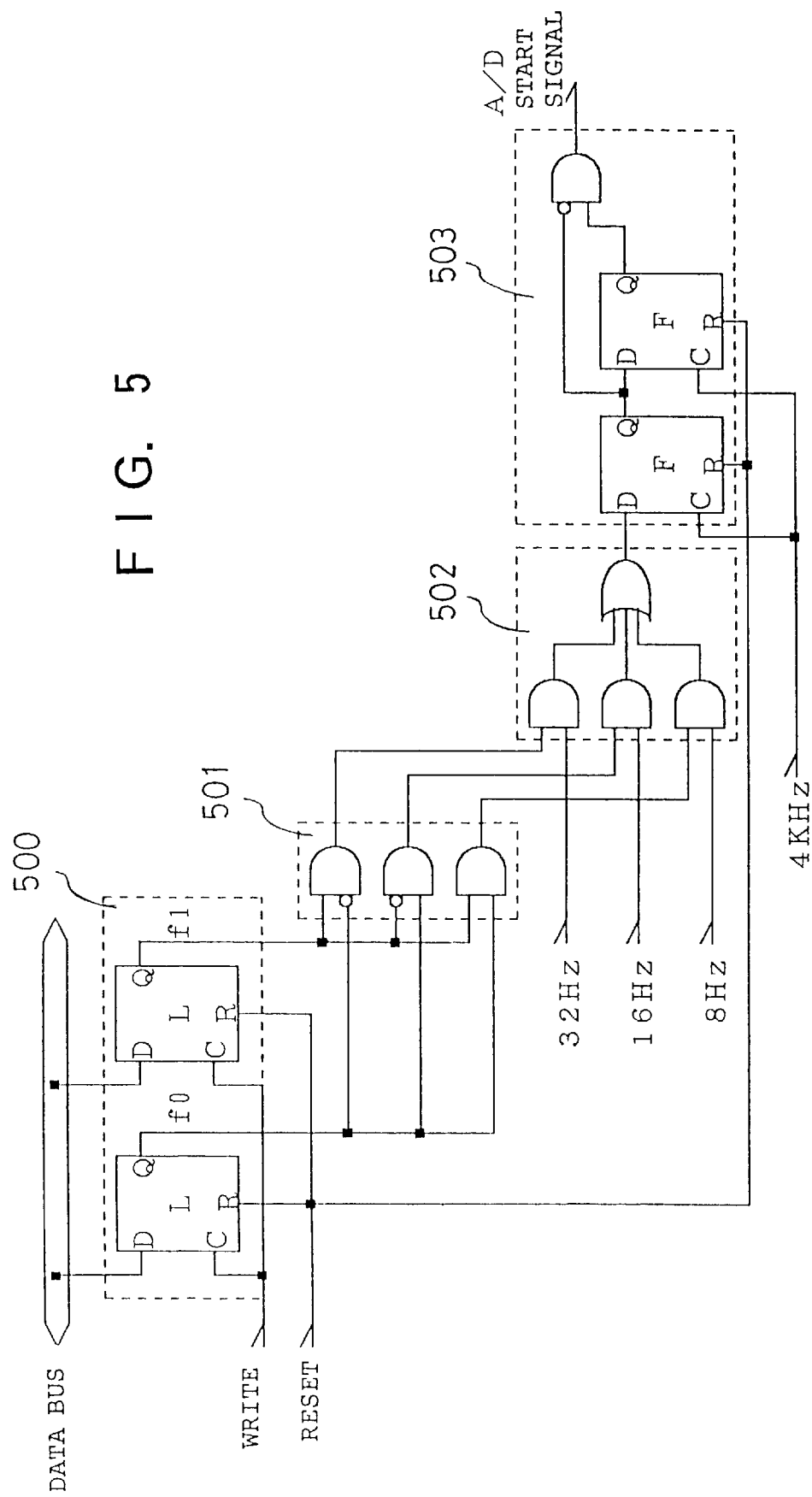
FIG. 5 is a circuit diagram of an operation frequency setting circuit in the biosignal display apparatus of the embodiment of the invention.

FIG. 5 is a specific circuit embodiment of the operation frequency setting circuit 406 shown in FIG. 4. A 2-bit frequency setting register 500 is a register for setting the operation frequency of the A/D converter 402. Data sent from the CPU 408 is written to the register 500. Selection among an 8-Hz signal, a 16-Hz signal and a 32-Hz signal that are supplied from the timing generating circuit 404 is performed by using an output signal of the register 500 and gate circuits 501 and 502. A start signal generating circuit 503 generates an A/D start signal at the frequency of the selected signal, and supplies it to the A/D converter 402.

Now, a detailed description will be made of the timing at which the frequency data is sent from the CPU 408 to the operation frequency setting circuit 406 and the operations in which the FFT calculation is performed by the FFT processor 409 and a result is displayed on the display device 410 as the number of pulses.

Figure 8:
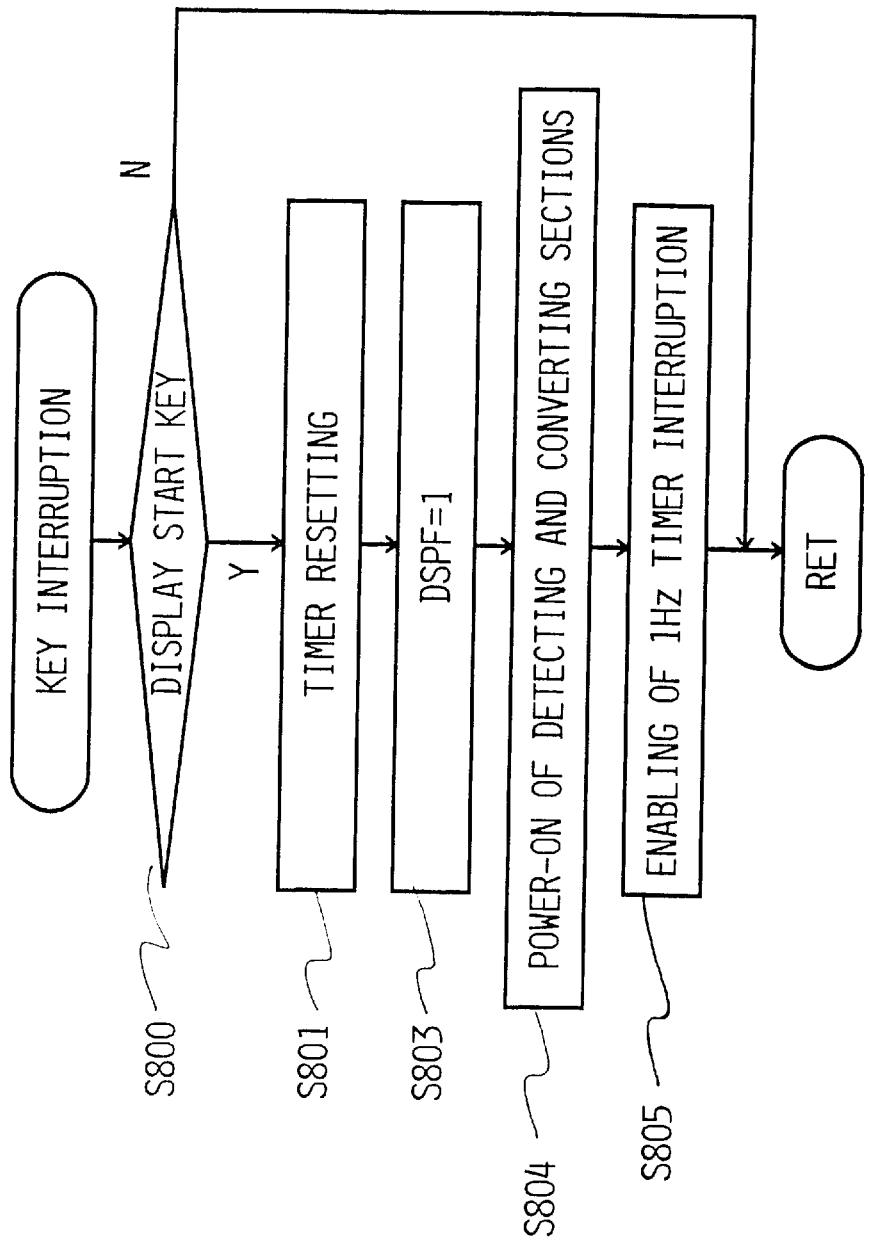
FIG. 8 is a flowchart showing key interrupt processing of a CPU in the biosignal display apparatus of the embodiment of the invention.

FIG. 8 is a flowchart showing interrupt processing of the CPU 408 which is performed when the switch 405 is operated. At the beginning of the interrupt processing, it is judged whether the switch to effect display has been operated (S800). If it is judged that the switch to start display has been operated, the timing generating circuit 404 is reset to control the timing correctly (S801). A DSP flag to be used in a branching condition of 1-Hz interrupt processing (described below) is set at 1 (S803). Then, power is supplied to the pulse wave sensor 400, amplifier circuit 401 and A/D converter 402, which are analog circuits (S804). To performing counting for the operation stabilizing time of those analog circuits, the CPO 408 enables a 1-Hz interrupt signal to be sent from the timing generating circuit 404 (S805).

Figure 9:
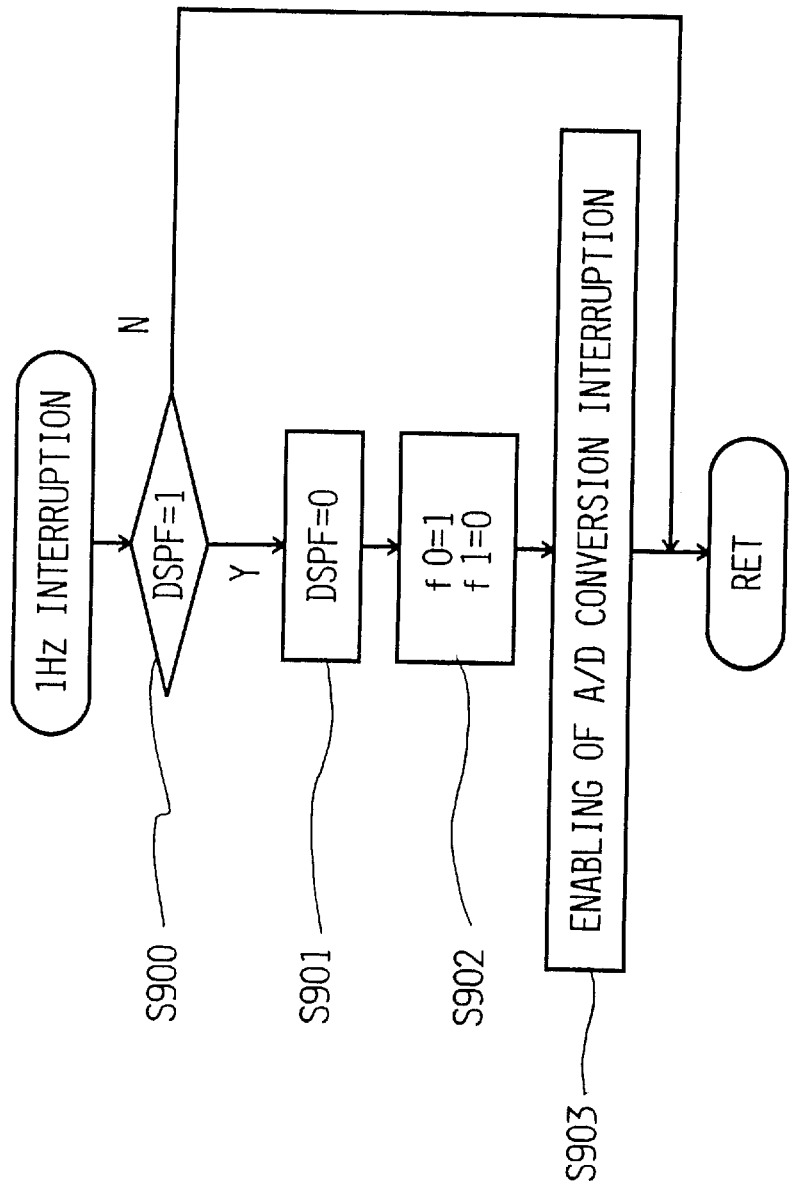
FIG. 9 is a first flowchart showing 1-Hz interrupt processing of the CPU in the biosignal display apparatus of the embodiment of the invention.

FIG. 9 is a flowchart showing the 1-Hz interrupt processing for performing counting for the operation stabilizing time of the analog circuits and initial setting of the A/D conversion. First, the DSP flag that has been set in the key interrupt processing is checked (S900). If it has been set, it is now reset (S901). Although in this embodiment the operation stabilizing time of the analog circuits is set at 1 second, the counting may be performed for several seconds by using a counter or the like if 1 second is not enough. To set, at 32 Hz the first operation interval of the A/D converter 402, data (f0=1, f1=0) are written to the register 500 (S902). Finally, A/D conversion end interruption is enabled (S903), and the process returns to the main routine.

Figure 7:
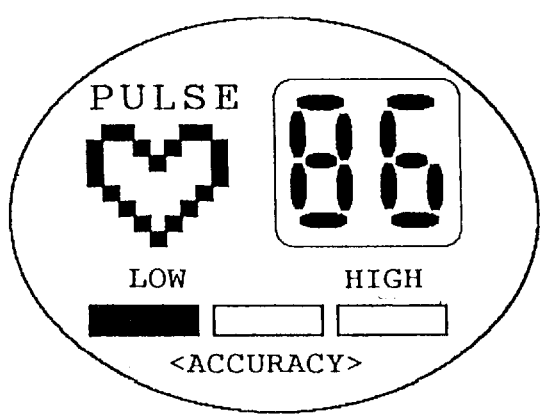
FIG. 7 illustrates an example of display in the biosignal display apparatus of the embodiment of the invention.
Figure 10:
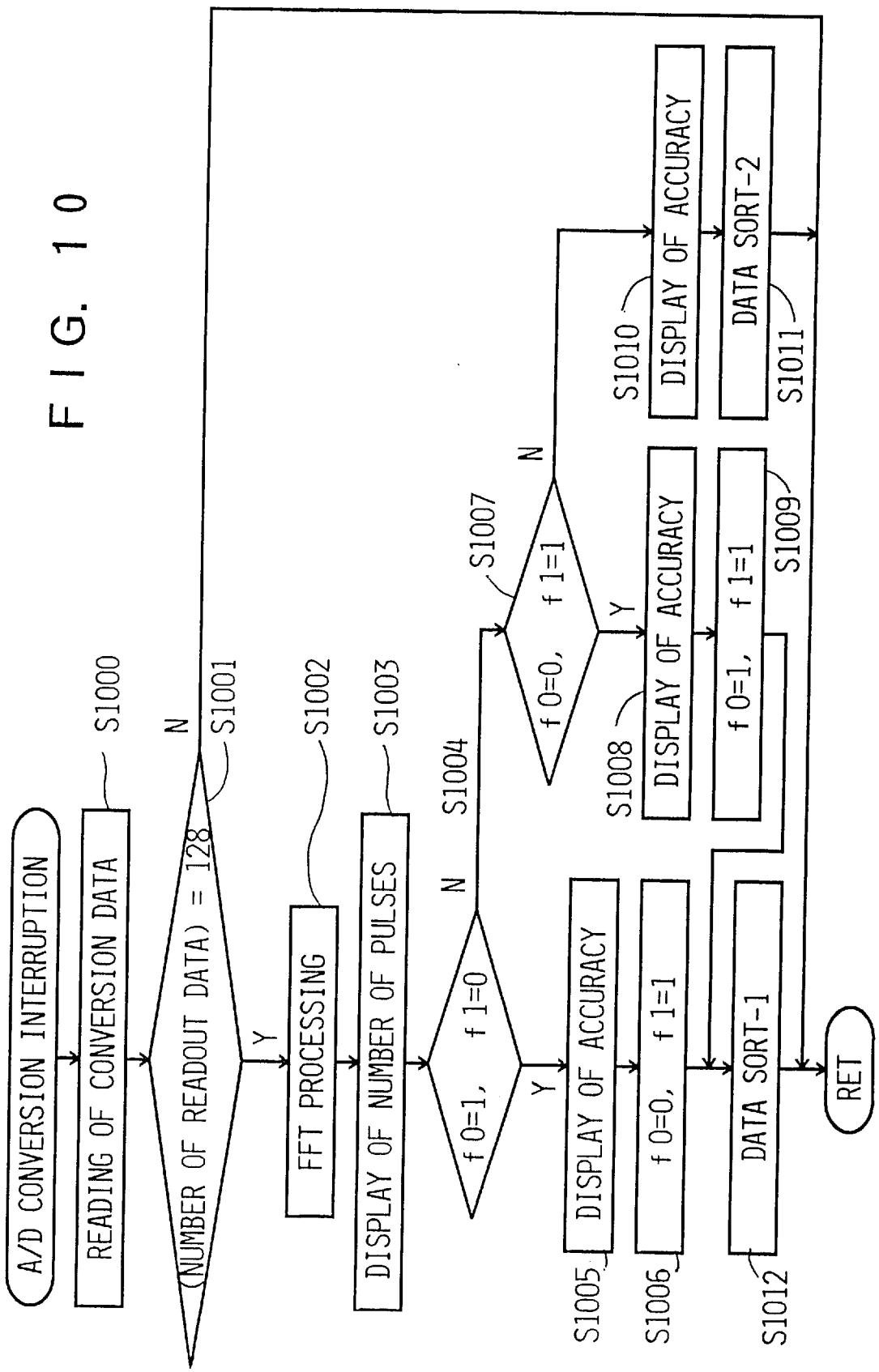
FIG. 10 is a flowchart showing A/D Conversion interrupt processing of the CPU in the biosignal display apparatus of the invention.

FIG. 10 is a flowchart showing processing on the A/D conversion end interrupt signal. In response to A/D conversion interruption, the CPU 408 reads conversion data from the A/D converter 402 and stores it into the RAM 408 (S1000). In doing so, the CPU 408 judges whether the number of readout and stored data has reached 128 (S1000). If the number of stored data has reached 128, the CPU 408 transfers the data from the RAM 407 to the FFT processor 409 and supplies a FFT calculation instruction to the FFT processor 409, to have it perform FFT calculation (S1000). The CPU 408 then calculates the number of pulses per minute from frequency components of pulse waves which result from the FFT calculation, and transfers the calculated number to the display device 410 to have it display the calculated number (S1003). Then, the CPU 408 changes the A/D operation frequency data that is set in the operation frequency setting circuit 406. The CPU 408 judges whether the setting number is equal to 32 Hz (f0=1, f1=0) (S1004). If the judgment result is affirmative, the CPU 408 causes the display device 410 to perform accuracy display as shown in FIG. 7 (S1005). Where the operation interval data is 32 Hz (f0=1, f1=0), in which case the accuracy of the number-of-pulse calculation is lowest, one segment is lighted as shown in FIG. 7. Thereafter, the CPU 408 changes the operation interval to 16 Hz (f0=0, f1=1) (S1006). In doing so, the CPU 408 performs data sort-1, because if all the data stored during the 32-Hz (f0=1, f1=0) setting are erased, it takes 8 seconds to convert 128 data next time (S1012).

Figure 11:
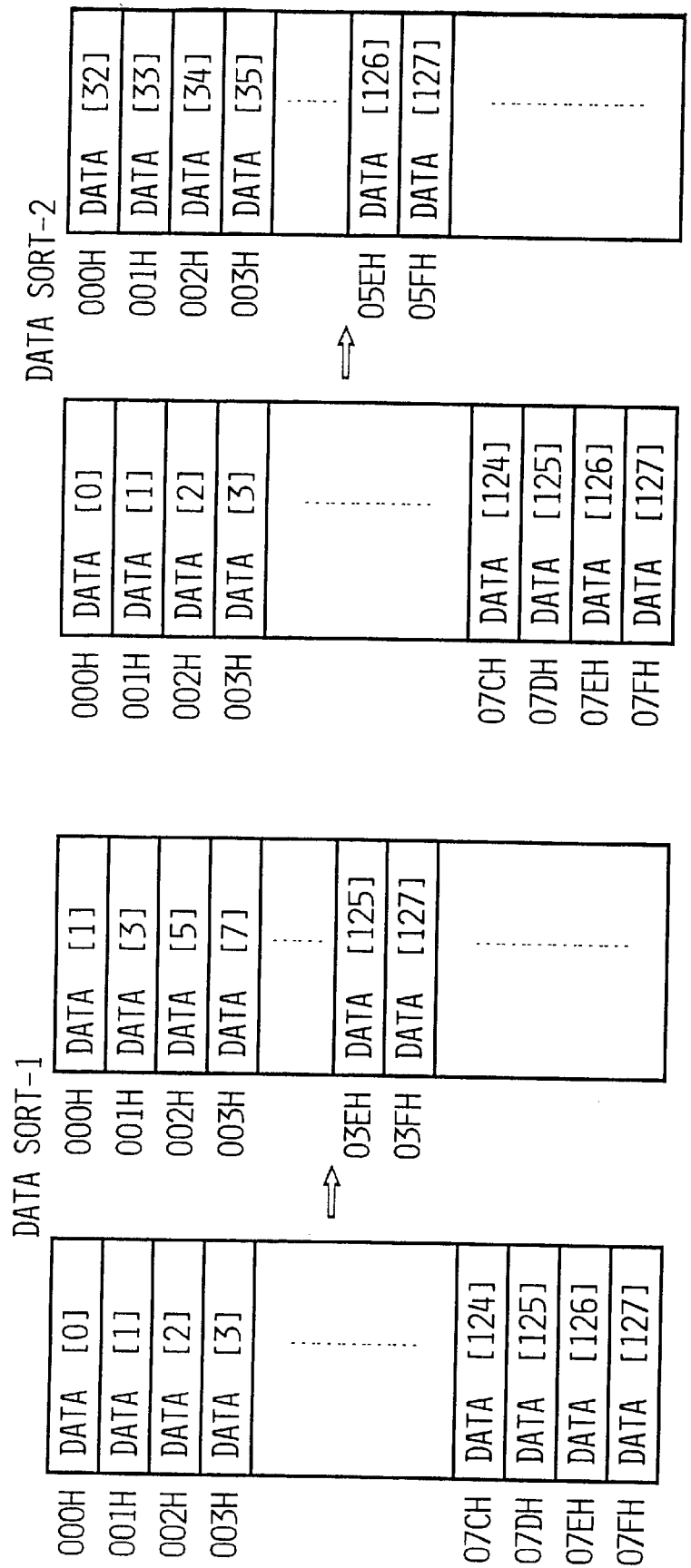
FIG. 11 illustrates a data sorting method of the CPU in the biosignal display apparatus of the invention.

FIG. 11 shows a sorting method of data sort-1. Even-numbered conversion data of 32 Hz (f0=1, f0=0) are erased and odd-numbered data are rearranged in the original order. Resulting data can serve as 64 data of 16 Hz (f0=0, f1=1) already stored.

By performing operations similar to the above, the CPU 408 judges whether the setting value is 16 Hz (f0=0, f1=1) (S1007). If the judgment result is affirmative, the CPU 408 causes the display device 410 to perform accuracy display (S1008). In the case of 16 Hz (f0=0, f0=1), two segments in FIG. 7 are lighted. The CPU 408 then changes the operation interval to 8 Hz (f0=1, f1=1) (S1009), and performs data sort-1 again (S1012).

If the setting value has already been made 8 Hz (f0=1, f1=1), the CPU 408 performs data sort-2 (S1011) after lighting three segments in FIG. 7 (S1010). As shown in FIG. 11, in a sorting method of data sort-2, 32 data from the head are erased and the remaining data are rearranged in the original order. By virtue of this sorting, 128 data will be stored again after 4 seconds and the number of pulses will be displayed.

Figure 6:
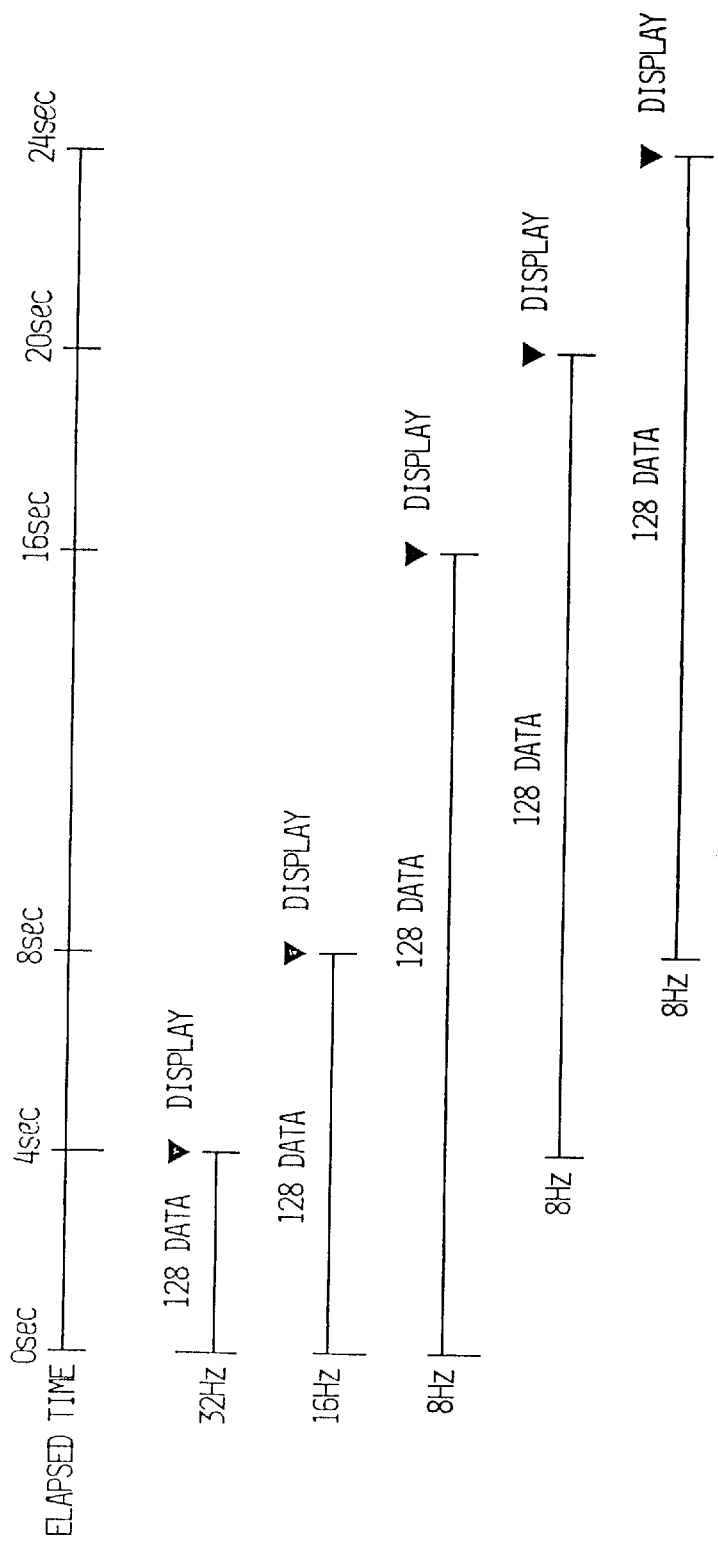
FIG. 6 illustrates operation frequencies and display timing in the biosignal display apparatus of the embodiment of the invention.

FIG. 6 shows the operation intervals of the A/D converter 402 and the display timing. The converting operation is performed at 32 Hz during the first 4 seconds. By performing data sort-1, the converting operation is performed at 16 Hz during the next 4 seconds. The converting operation is performed at 8 Hz during the next 8 seconds. As for the FFT calculation and the display timing, the first calculation result is displayed after a lapse of 4 seconds, the second calculation result is displayed after a further lapse of 4 seconds, and the third calculation result is displayed after a further lapse of 8 seconds. Thereafter, the calculation result display is switched every 4 seconds. The calculation accuracy of the number of pulses is improved as the operation interval of the A/D converter 402 becomes longer from 32 Hz to 16 Hz, and to 8 Hz. By performing the above operations, results can be displayed quickly while the accuracy is improved gradually.

(2) Second Embodiment

In the first embodiment, the method of quickly displaying results is such that the operation frequency of the A/D converter 402 is varied in time series order and the FFT calculation is performed and display is effected when 128 data values have been stored in the RAM 407. In the second embodiment, for the same purpose of quickly displaying results, before the number of data values stored in the RAM 407 reaches 128, those data are subjected to the FFT calculation together with initializing data and display is effected.

Figure 12:
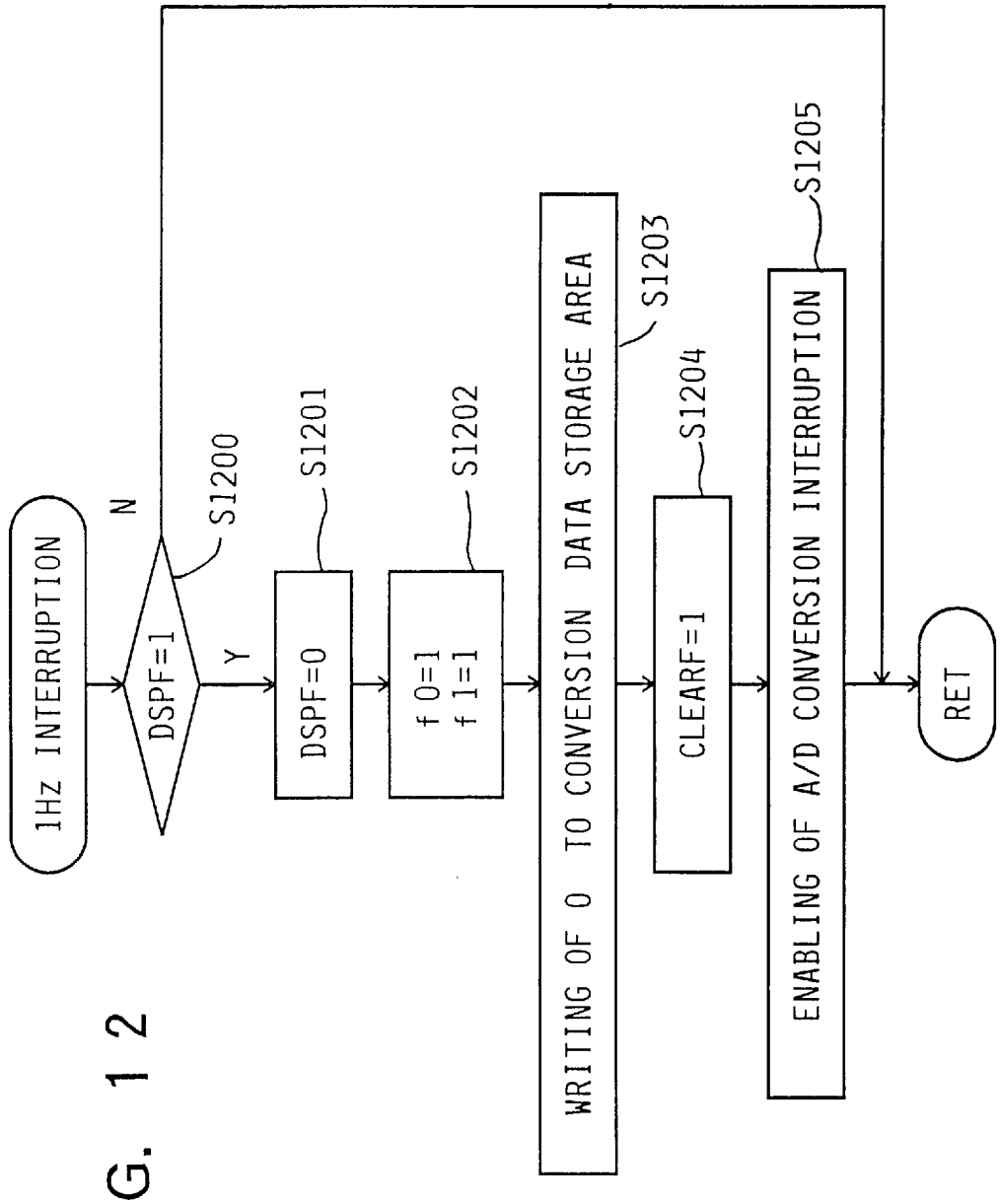
FIG. 12 is a second flowchart showing 1-Hz interrupt processing of a CPU in a biosignal display apparatus of another embodiment of the invention.

A biosignal display apparatus according to the second embodiment of the invention will be described with reference to the functional block diagram of FIG. 4 and operation flowcharts of FIGS. 12 and 13.

When the switch 405 is operated, a display start signal is supplied to the CPU 408 as an interrupt signal. Switch interrupt processing of the CPU 408 is the same as in the first embodiment. FIG. 12 is a second flowchart showing 1-Hz interrupt processing to perform initial setting of the RAM 407 and the A/D conversion. First, the DSP flag is checked which has been set in the key interrupt processing shown in FIG. 8 (S1200). If the DSP flag has been set, it is now reset (S1201). Then, to set the operation frequency of the A/D converter at 8 Hz, data (f0=1, f1=1) is written to the register 500 (S1202). While in the first embodiment the data of the register 500 is varied in time series order, it is fixed in this embodiment. The reason why the operation interval is made 8 Hz is that if pulse waves are observed continuously, frequency components are distributed from the DC component to 4 Hz. Then, to initialize conversion data, 0 is written to a conversion data storage area secured in the RAM 407 (S1203). The conversion data is stored as sign-added data in the RAM 407, in which a half of the maximum value of the A/D converter 402 is stored as 0. Then, a CLEAR flag is set which will be used in the A/D conversion interrupt processing (S1204), A/D conversion interruption is enabled (S1205), and the process returns to the main routine.

Figure 13:
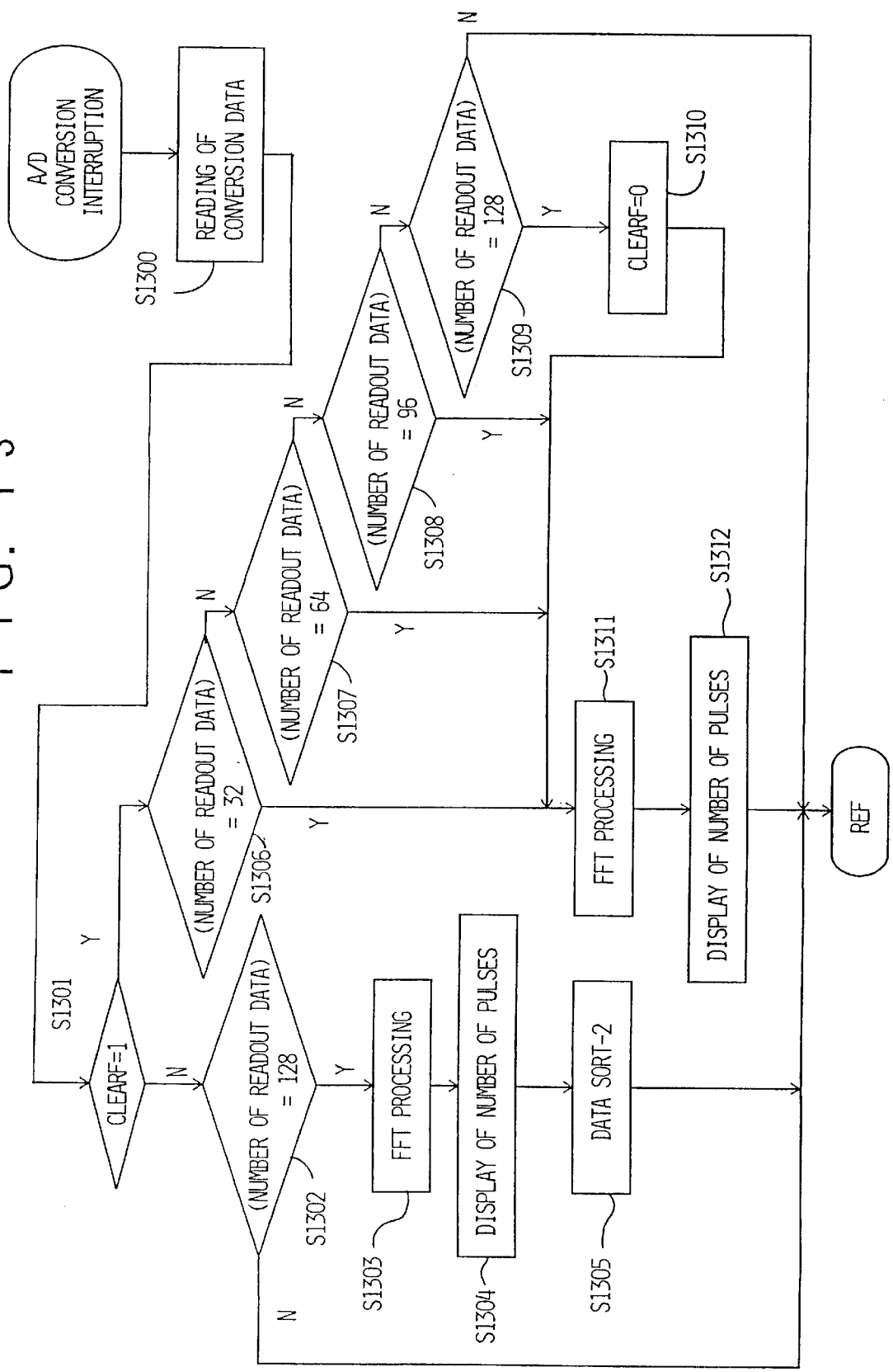
FIG. 13 is a flowchart showing A/D conversion interrupt processing of the CPU in the biosignal display apparatus of the invention.

FIG. 13 is a second flowchart showing the A/D conversion interrupt processing. In the first step of the interrupt processing, the CPU 408 reads conversion data from the A/D converter 402 and stores it into the RAM 407 (S1300). The CPU 408 checks the CLEAR flag which has been set in the 1-Hz interrupt processing (S1301). If it has been set, the CPU 408 checks the number of stored data. When the number of data stored in the RAM 407 has reached 32 for the first time, the CPU 408 supplies a FFT calculation instruction to the FFT processor 409 to have it perform FFT processing (S1311). The CI?U 408 calculates the number of pulses from its result and causes the number to be displayed (S1312). In this case, the newly stored 32 data and the 96 data that have been initialized to 0 are subjected to the calculation. Subsequently, FFT processing is performed (S1311) in the similar manner when the number of data stored in the RAM 407 reaches 64 (S1307), 96 (S1308) and 128 (S1309). The four times of FFT processing (S1311) are performed at timings 4, 8, 12 and 16 seconds after the initializing data 0 is written to the RAM 407. For every FFT processing, the number of pulses is displayed on the display device 410 as a result of the calculation. When 128 data have been stored for the first time, the CLEAR flag is reset (S1310). Upon resetting of the CLEAR flag, FFT processing is performed at every time when 128 data are stored (S1303). Based on a result of the FFT processing, the number of pulses is calculated and displayed (S1304).

Finally, by performing data sort-2 as shown in FIG. 11, the number of pulses can be displayed on the display device 410 every 4 seconds.

Figure 14:
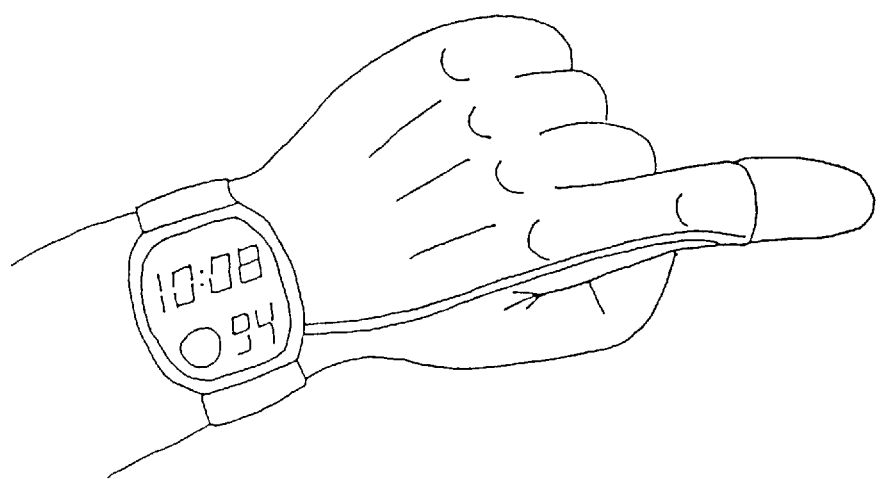
FIG. 14 shows the appearance of a biosignal display apparatus of the invention.

FIG. 14 shows an appearance of the biosignal display apparatus of the invention. A finger tip pulse wave is detected by incorporating a pulse wave sensor in a finger sack and connecting a signal line to a watch main body circuit board via a lead wire and a connector.

As described above, according to the biosignal display apparatus of the invention, when biosignal detection results are displayed based on the frequency-domain analysis in the beginning, the results can be displayed quickly while the accuracy is improved gradually. Therefore, the invention can provide the easy-to-use biosignal display apparatus which does not cause a user to be in doubt of the display data.

What is claimed is:

1. A biosignal display apparatus comprising: a biosignal detecting means having a sensor for detecting a biosignal and producing a corresponding output; a biosignal converting means for converting the output from the biosignal detecting means into a digital biosignal; a biosignal storing means for storing successively converted digital biosignal values; a biosignal calculating means for analyzing the digital biosignal values in the frequency domain when the number of digital biosignal data values stored in the biosignal storing means has reached a predetermined number; a display means for displaying the calculation results of the biosignal calculating means; an input means for generating a start signal of a biosignal measurement in response to an external input operation; a timing signal generating means for generating a timing signal in response to a basic clock signal; and an operation frequency control means for progressively changing a sampling frequency of the biosignal converting means in a time series manner based on the start signal generated by the input means and the timing signal generated by the timing signal generating means.

2. A biosignal display apparatus according to claim 1; wherein the timing signal generating means includes means for generating the timing signal a predetermined period of time after receiving the start signal generated by the input means.

3. A biosignal display apparatus according to claim 1; wherein the display means includes means for displaying a relative accuracy of the calculation results of the biosignal calculating means.

4. A biosignal display apparatus comprising: a biosignal detecting means having a sensor for detecting a biosignal and producing a corresponding output; a biosignal converting means for converting the output from the biosignal detecting means into a digital biosignal; a biosignal storing means for storing successively converted digital biosignal values; a biosignal calculating means for analyzing the digital biosignal values in the frequency domain; a display means for displaying the calculation results of the biosignal calculating means; an input means for generating a start signal of a biosignal measurement in response to an external input operation; an initializing means for initializing the digital biosignal values stored in the biosignal storing means in response to the start signal genera-ed by the input means; a timing signal generating means for generating a timing signal in response to a basic clock signal an operation frequency setting means for setting a sampling frequency of the biosignal converting means based on the timing signal generated by the timing signal generating means; and a calculation control means for progressively changing, in a time series manner, a number of digital biosignal values to be subjected to frequency-domain analysis in response to the start signal generated by the input means and the timing signal generated by the timing signal generating means.

5. A biosignal display apparatus according to claim 4; wherein the timing signal generating means includes means for generating the timing signal a predetermined period of time after receiving the start signal generated by the input means.

6. A biosignal display apparatus according to claim 4; wherein the display means includes means for displaying a relative accuracy of the calculation results of the biosignal calculating means.

7. A biosignal display apparatus according to claim 4; wherein the biosignal storing means includes means for storing the digital biosignal values as sign-added data having a central value of 0, and the initializing means includes means for initializing all the digital biosignal values stored in the biosignal storing means to 0 (zero) in response to the start signal generated by the input means.

8. A biosignal display apparatus comprising: a biosignal detecting means having a sensor for detecting a biosignal and producing a corresponding output; a biosignal converting means for converting the output from the biosignal detecting means into a digital biosignal; biosignal storing means for storing successively converted digital biosignal values; biosignal calculating means for analyzing the digital biosignal values in the frequency domain when the number of digital biosignal values stored in the biosignal storing means has reached a predetermined number; display means for displaying the calculation results of the biosignal calculating means; input means for generating a start signal of a biosignal measurement in response to an external input operation; initializing means for initializing the digital biosignal values stored in the biosignal storing means in response to the start signal generated by the input means; timing signal generating means for generating a timing signal in response to a basic clock signal, operation frequency setting means for setting a sampling frequency of the biosignal converting means based on the timing signal generated by the timing signal generating means; and calculation control means for progressively changing, in a time series manner, a number of digital biosignal values to be subjected to frequency-domain analysis in response to the start signal generated by the input means and the timing signal generated by the timing signal generating means; wherein the biosignal storing means includes means for storing the digital biosignal values as sign-added data having a central value of 0, and the initializing means includes means for initializing all the digital biosignal values stored in the biosignal storing means to 0 (zero) in response to the start signal generated by the input means.

9. A biosignal display apparatus comprising: detecting means for detecting a biosignal and producing a corresponding output signal; an analog-to-digital converter for converting the output signal into digital biosignal data values; frequency analyzing means for analyzing a predetermined number of the digital biosignal data values in the frequency domain; frequency control means for selectively varying the sampling frequency of the analog-to-digital converter to progressively increase the accuracy of the frequency analysis; and display means for displaying a result of the frequency analysis.

10. A biosignal display apparatus according to claim 9; wherein the frequency control means comprises an oscillator for generating a basic clock signal, a divider for frequency dividing the basic clock signal and producing a plurality of timing signals each having a different frequency, frequency selecting means for selecting one of the timing signals to drive the analog-to-digital converter, and frequency control means for controlling the frequency selecting means to progressively select a lower frequency one of the timing signals on a time series basis so as to progressively increase the accuracy of the frequency analysis.

11. A biosignal display apparatus according to claim 10; wherein the display means further comprises means for displaying a relative accuracy of the frequency analysis.

12. A biosignal display apparatus according to claim 11; wherein the means for displaying a relative accuracy comprises means for driving a singles display element when a highest frequency timing signal is selected, and means for driving additional ones of a series of display elements when timing signals having a lower frequency are progressively selected.

13. A biosignal display apparatus according to claim 9; further comprising input means for producing a start signal to commence a biosignal measuring operation; and control means for enabling the analog-to-digital converter, the frequency analyzing means and the frequency control means in response to the start signal.

14. A biosignal display apparatus according to claim 13; further comprising stabilizing means for delaying operation of the analog-to-digital converter, the frequency analyzing means and the frequency control means for a predetermined time after detection of the start signal so as to permit stabilization of the analog-to-digital converter, the frequency analyzing means and the frequency control means.

15. A biosignal display apparatus according to claim 9; further comprising means for generating a start signal to commence a biosignal measurement; and wherein the frequency control means includes means responsive to the start signal for initially setting the sampling frequency of the analog-to-digital converter at a first frequency to permit a rapid initial display of a biosignal measurement and for progressively reducing the sampling frequency of the analog-to-digital converter on a time series basis so as to progressively increase the accuracy of the measurement.

16. A biosignal display apparatus according to claim 15; further comprising a memory for storing the digital biosignal data values; and initializing means for initializing the memory in response to a change in sampling frequency of the analog-to-digital converter.

17. A biosignal display apparatus according to claim 16; wherein the initializing means includes means for erasing all digital biosignal data values stored in even-numbered memory locations and rearranging consecutively the remaining data when the sampling frequency of the analog-to-digital converter is changed from a first frequency to a second frequency equal to one-half the first frequency, such that the predetermined number of digital biosignal data values may be acquired more rapidly.

18. A biosignal display apparatus comprising: detecting means for detecting a biosignal and producing a corresponding output signal; an analog-to-digital converter for converting the output signal into digital biosignal data values; frequency analyzing means for analyzing a predetermined number of the digital biosignal data values in the frequency domain; control means for selectively varying the predetermined number off digital biosignal data values on a time series basis so as to progressively increase the accuracy of the frequency analysis; and display means for displaying a result of the frequency analysis.

19. A biosignal display apparatus according to claim 18; wherein the display means further comprises means for displaying a relative accuracy of the frequency analysis.

20. A biosignal display apparatus according to claim 19; wherein the means for displaying a relative accuracy comprises a series of display elements; and means for driving a single display element when the predetermined number of digital biosignal data values is a smallest value and means for driving additional ones of the series of display elements as the predetermined number is progressively increased.

21. A biosignal display apparatus according to claim 18; further comprising input means for producing a start signal to commence a biosignal measuring operation; and control means for enabling the analog-to-digital converter, the frequency analyzing means and the control means in response to the start signal.

22. A biosignal display apparatus according to claim 21; further comprising stabilizing means for delaying operation of the analog-to-digital converter, the frequency analyzing means and the control means for a predetermined time after detection of the start signal so as to permit stabilization of the analog-to-digital converter, the frequency analyzing means and the control means.

23. A biosignal display apparatus according to claim 18; further comprising means for generating a start signal to commence a biological measurement; and wherein the control means includes means responsive to the start signal for initially setting the predetermined number at a first value to permit a rapid initial display of a biological measurement and for progressively increasing the predetermined number on a time series basis so as to progressively increase the accuracy of the measurement.

* * * * *

UNITED STATES PATENT AND TRADEMARK OFFICE
CERTIFICATE OF CORRECTION

PATENT NO.   : 5,857,465
DATED        : January 12, 1999
INVENTOR(S)  : NAKAMURA et al.

It is certified that error appears in the above-indentified patent and that said Letters Patent is hereby corrected as shown below:

On the title page, item [30], insert the following:

--Foreign Application Priority Data August 17, 1994

[JP] Japan...6-193413--.

Signed and Sealed this

Fifteenth Day of February, 2000

*Attest:*

*Attesting Officer*

Q. TODD DICKINSON

*Commissioner of Patents and Trademarks*